United States Patent
Lin et al.

(10) Patent No.: US 9,775,547 B2
(45) Date of Patent: *Oct. 3, 2017

(54) SYSTEM AND METHOD FOR STORING AND PROVIDING PATIENT-RELATED DATA

(71) Applicant: Covidien LP, Mansfield, MA (US)

(72) Inventors: Andy S. Lin, Boulder, CO (US); Bo Chen, Louisville, CO (US); Friso Schlottau, Lyons, CO (US)

(73) Assignee: Covidien LP, Mansfield, MA (US)

( * ) Notice: Subject to any disclaimer, the term of this patent is extended or adjusted under 35 U.S.C. 154(b) by 149 days.

This patent is subject to a terminal disclaimer.

(21) Appl. No.: 14/931,393

(22) Filed: Nov. 3, 2015

(65) Prior Publication Data

US 2016/0051172 A1 Feb. 25, 2016

Related U.S. Application Data

(63) Continuation of application No. 13/406,118, filed on Feb. 27, 2012, now Pat. No. 9,192,330.

(51) Int. Cl.
*A61B 5/1455* (2006.01)
*A61B 5/00* (2006.01)

(52) U.S. Cl.
CPC ........ *A61B 5/14552* (2013.01); *A61B 5/7278* (2013.01); *A61B 5/742* (2013.01); *A61B 5/7475* (2013.01); *A61B 5/002* (2013.01); *A61B 5/14553* (2013.01); *A61B 5/6814* (2013.01); *A61B 2560/0475* (2013.01); *A61B 2562/04* (2013.01)

(58) Field of Classification Search
None
See application file for complete search history.

(56) References Cited

U.S. PATENT DOCUMENTS

| | | |
|---|---|---|
| 4,281,645 A | 8/1981 | Jobsis |
| 5,139,025 A | 8/1992 | Lewis et al. |
| 5,140,989 A | 8/1992 | Lewis et al. |
| 5,217,013 A | 6/1993 | Lewis et al. |
| 5,349,961 A | 9/1994 | Stoddart et al. |
| 5,465,714 A | 11/1995 | Scheuing |
| 5,477,853 A | 12/1995 | Farkas et al. |
| 5,482,034 A | 1/1996 | Lewis et al. |
| 5,584,296 A | 12/1996 | Cui et al. |
| 5,645,059 A | 7/1997 | Fein et al. |
| 5,697,367 A | 12/1997 | Lewis et al. |
| 5,795,292 A | 8/1998 | Lewis et al. |
| 5,902,235 A | 5/1999 | Lewis et al. |

(Continued)

FOREIGN PATENT DOCUMENTS

WO 2008/020845 2/2008

OTHER PUBLICATIONS

INVOS System Specifications; Somanetics Cerebral/Somatic Invos Oximeter Reflecting the Color of Life; 2008, pp. 1-2, Somanetics Corporation, Troy, Michigan.

*Primary Examiner* — Eric Winakur
*Assistant Examiner* — Marjan Fardanesh
(74) *Attorney, Agent, or Firm* — Fletcher Yoder PC (57) ABSTRACT

According to various embodiments, a regional oximetry sensor may include a light emitting element configured to emit light, a light detector configured to receive the light, and a memory device configured to store a baseline. The baseline stored by the memory device enables a regional oximetry monitor to display the baseline on a display of the regional oximetry monitor.

20 Claims, 4 Drawing Sheets

(56) References Cited

U.S. PATENT DOCUMENTS

| | | |
|---|---|---|
| 6,125,296 A | 9/2000 | Hubelbank |
| 6,463,310 B1 | 10/2002 | Swedlow et al. |
| 6,553,241 B2 | 4/2003 | Mannheimer et al. |
| 6,591,123 B2 | 7/2003 | Fein et al. |
| 6,600,940 B1 | 7/2003 | Fein et al. |
| 6,606,510 B2 | 8/2003 | Swedlow et al. |
| 6,615,065 B1 | 9/2003 | Barrett et al. |
| 6,628,975 B1 | 9/2003 | Fein et al. |
| 6,675,031 B1 | 1/2004 | Porges et al. |
| 6,708,049 B1 | 3/2004 | Berson et al. |
| 6,801,797 B2 | 10/2004 | Mannheimer et al. |
| 7,668,588 B2 | 2/2010 | Kovacs |
| 7,910,875 B2 | 3/2011 | Al-Ali |
| 7,983,729 B2 | 7/2011 | Mannheimer et al. |
| 9,161,722 B2 | 10/2015 | Besko |
| 2004/0024297 A1 | 2/2004 | Chen et al. |
| 2006/0020179 A1 | 1/2006 | Anderson et al. |
| 2007/0049810 A1 | 3/2007 | Mannheimer et al. |
| 2007/0106172 A1 | 5/2007 | Abreu |
| 2007/0150017 A1 | 6/2007 | Salo |
| 2008/0177163 A1 | 7/2008 | Wang et al. |
| 2008/0316488 A1 | 12/2008 | Mao et al. |
| 2009/0163783 A1 | 6/2009 | Mannheimer et al. |
| 2011/0066015 A1 | 3/2011 | Swedlow et al. |
| 2011/0112379 A1 | 5/2011 | Li et al. |
| 2011/0172743 A1 | 7/2011 | Davis et al. |
| 2011/0190600 A1 | 8/2011 | McKenna et al. |
| 2013/0079618 A1 | 3/2013 | Sandmore |

SYSTEM AND METHOD FOR STORING AND PROVIDING PATIENT-RELATED DATA

CROSS-REFERENCE TO RELATED APPLICATION

This application is a continuation of U.S. application Ser. No. 13/406,118, filed Feb. 27, 2012, the disclosure of which is hereby incorporated by reference in its entirety for all purposes.

BACKGROUND

The present disclosure relates generally to sensors and, more particularly, to sensors configured to store and provide patient-related data.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide variety of devices have been developed for non-invasively monitoring physiological characteristics of patients. For example, an oximetry sensor system may non-invasively detect various patient blood flow characteristics, such as the blood-oxygen saturation of hemoglobin in blood, the volume of individual blood pulsations supplying the tissue, and/or the rate of blood pulsations corresponding to each heart beat of a patient. During operation, the oximeter sensor emits light and photoelectrically senses the absorption and/or scattering of the light after passage through the perfused tissue. A photo-plethysmographic waveform, which corresponds to the cyclic attenuation of optical energy through the patient's tissue, may be generated from the detected light. Additionally, one or more physiological characteristics may be calculated based upon the amount of light absorbed or scattered. More specifically, the light passed through the tissue may be selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

For example, a reflectance-type sensor placed on a patient's forehead may emit light into the site and detect the light that is "reflected" back after being transmitted through the forehead region. The amount of light detected may provide information that corresponds to valuable physiological patient data. The data collected by the sensor may be used to calculate one or more of the above physiological characteristics based upon the absorption or scattering of the light. For instance, the emitted light is typically selected to be of one or more wavelengths that are absorbed or scattered in an amount related to the presence of oxygenated versus de-oxygenated hemoglobin in the blood. The amount of light absorbed and/or scattered may be used to estimate the amount of the oxygen in the tissue using various algorithms.

The sensors generally include one or more emitters that emit the light and one or more detectors that detect the light. The emitters and detectors may be housed in a reusable or disposable oximeter sensor that couples to the oximeter electronics and the display unit (hereinafter referred to as the monitor). The monitor may collect historical physiological data for the patient, which may be used by a clinician or medical personnel for diagnostic and monitoring purposes. Patients are often moved to various locations during treatment. For example, a patient may be transported in an ambulance, delivered to an emergency room, moved to an operating room, transferred to a surgical recovery room, transferred to an intensive care unit, and then moved to a nursing floor or other locations. Thus, the patient may be moved between various locations within the same hospital, or between different hospitals. The sensor employed to monitor the condition of the patient may be adhesive in its attachment and remain with the patient. The monitors, however, may be local to particular locations within a facility or vehicle. Thus, the sensor may be disconnected from the monitor at a departure site and reconnected to another monitor at a destination site. Consequently, patient-related data (e.g., historical physiological data) collected by the monitor at the departure site may be unavailable to the clinician attending the patient at the destination site.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Also, as used herein, the term "over" or "above" refers to a component location on a sensor that is closer to patient tissue when the sensor is applied to the patient.

The present embodiments relate to sensors that may be used to store and provide one or more physiological characteristics of a patient, such as a regional oxygen saturation ($rSO_2$) baseline. A baseline may refer to a line that is used as a base or reference for comparisons. For example, a caregiver may compare the condition of the patient before and after a medical procedure by referring to an $rSO_2$ baseline prepared prior to performing the procedure. The sensors described herein may incorporate one or more emitters and one or more detectors for determining the level of blood oxygen saturation in a particular region, such as a cerebral or somatic region, which may be referred to as regional oximetry. The regional oximetry sensors described herein may include a mechanism for storing and providing patient-related data, such as baselines, trend data, or other historical physiological data (e.g., blood oxygen saturation data for a patient). For example, the patient-related data may be provided from the sensor to a monitor coupled to the sensor. In certain embodiments, the data may be transmitted from the sensor to the monitor wirelessly. Use of $rSO_2$ baselines for comparisons may be more important with regional oximetry than with other types of oximetry because recommended values of $rSO_2$ may vary widely from patient to patient and depending on the condition of the patient. Thus, comparisons to $rSO_2$ baselines may be more valuable to the caregiver than comparisons to specific values of $rSO_2$ that may or may not apply to the particular patient or current condition of the patient.

In a specific embodiment, the patient-related data (e.g., $rSO_2$ baseline) is stored in the sensor that "travels" with the patient and is accessible wherever the patient is moved. This is achieved by storing the data within the sensor assembly. For example, the patient may be moved from a departure site to a destination site. At the destination site, a monitor or a device capable of interfacing with the sensor assembly may retrieve and display the data stored in the sensor. The stored data allows a clinician or medical personnel at the destination site to assess the condition of the patient for the entire time that the patient had been previously monitored. In addition, the clinician may use the stored data to compare the current condition of a patient to a condition before medical treatment or another procedure was performed. The present techniques may be used to store and provide various types of patient-related data including, but not limited to, $rSO_2$ baselines and other $rSO_2$ data.

By way of example, an INVOS® cerebral/somatic sensor, such as an OxyAlert™ NIR sensor by Somanetics Corporation or a SomaSensor® by Somanetics Corporation, which may include one or more emitters and a pair of detectors for determining site-specific oxygen levels, may represent such sensors. Example systems incorporating a sensor capable of performing regional oximetry and storing and providing patient-related data (e.g., $rSO_2$ baseline) are discussed with respect to FIGS. 1-3. Example methods for using these systems and sensors are discussed with respect to FIGS. 4 and 5.

Figure 1:
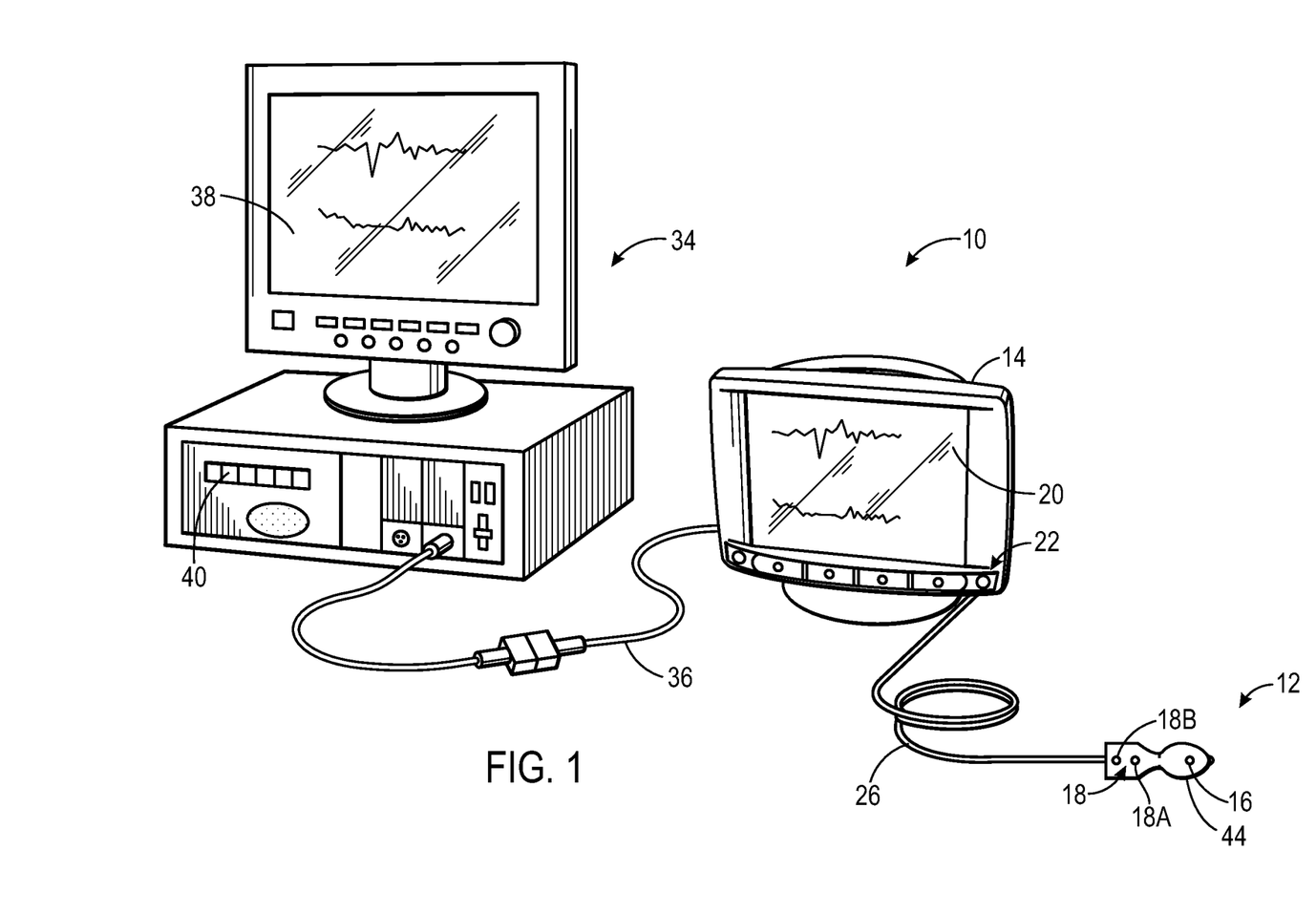
FIG. 1 is a front view of an embodiment of a monitoring system configured to be used with a sensor for regional saturation, in accordance with an aspect of the present disclosure.

With this in mind, FIG. 1 depicts an embodiment of a patient monitoring system 10 that may be used in conjunction with a medical sensor 12. Although the depicted embodiments relate to sensors for use on a patient's head, it should be understood that, in certain embodiments, the features of the sensor 12 as provided herein may be incorporated into sensors for use on other tissue locations, such as the back, the stomach, the heel, the ear, an arm, a leg, or any other appropriate measurement site. In addition, although the embodiment of the patient monitoring system 10 illustrated in FIG. 1 relates to photoplethysmography or regional oximetry, the system 10 may be configured to obtain a variety of medical measurements with a suitable medical sensor. For example, the system 10 may additionally be configured to determine patient electroencephalography (e.g., a bispectral index), or any other desired physiological parameter such as water fraction or hematocrit.

As noted, the system 10 includes the sensor 12 that is communicatively coupled to a patient monitor 14. Although only one sensor 12 is shown coupled to the monitor 14 in FIG. 1, in other embodiments, two, three, four, or more sensors 12 may be coupled to the monitor 14. For example, two sensors 12 may be used for cerebral oximetry and simultaneously two other sensors 12 used for somatic oximetry. As shown in FIG. 1, the sensor 12 includes an emitter 16 and a pair of detectors 18. The emitter 16 and detectors 18 of the sensor 12 are coupled to the monitor 14 via a cable 26 coupled to the monitor 14. The cable 26 may interface directly with the sensor 12 and may include a plurality of conductors (e.g., wires). As discussed below, the sensor 12 may be configured to store patient-related data, such as historical regional oximetry data (e.g., $rSO_2$ baseline).

The monitor 14 includes a monitor display 20 configured to display information regarding the physiological parameters monitored by the sensor 12, information about the system, and/or alarm indications. The monitor 14 may include various input components 22, such as knobs, switches, keys and keypads, buttons, etc., to provide for operation and configuration of the monitor 14. The monitor 14 also includes a processor that may be used to execute code, such as code for implementing various monitoring functionalities enabled by the sensor 12. As discussed below, for example, the monitor 14 may be configured to process signals generated by the detectors 18 to estimate the amount of oxygenated vs. de-oxygenated hemoglobin in a monitored region of the patient.

The monitor 14 may be any suitable monitor, such as an INVOS® System monitor available from Somanetics Corporation. Furthermore, to upgrade conventional operation provided by the monitor 14 to provide additional functions, the monitor 14 may be coupled to a multi-parameter patient monitor 34 via a cable 36 connected to a sensor input port. In addition to the monitor 14, or alternatively, the multi-parameter patient monitor 34 may be configured to calculate physiological parameters and to provide a central display 38 for the visualization of information from the monitor 14 and from other medical monitoring devices or systems. The multi-parameter monitor 34 includes a processor that may be configured to execute code. The multi-parameter monitor 34 may also include various input components 40, such as knobs, switches, keys and keypads, buttons, etc., to provide for operation and configuration of the a multi-parameter monitor 34. In addition, the monitor 14 and/or the multi-parameter monitor 34 may be connected to a network to enable the sharing of information with servers or other workstations.

In certain embodiments, the sensor 12 may be a wireless sensor 12. Accordingly, the wireless sensor 12 may establish a wireless communication with the patient monitor 14 and/or the multi-parameter patient monitor 34 using any suitable wireless standard. By way of example, the wireless module may be capable of communicating using one or more of the ZigBee standard, WirelessHART standard, Bluetooth standard, IEEE 802.11x standards, or MiWi standard.

Figure 2:
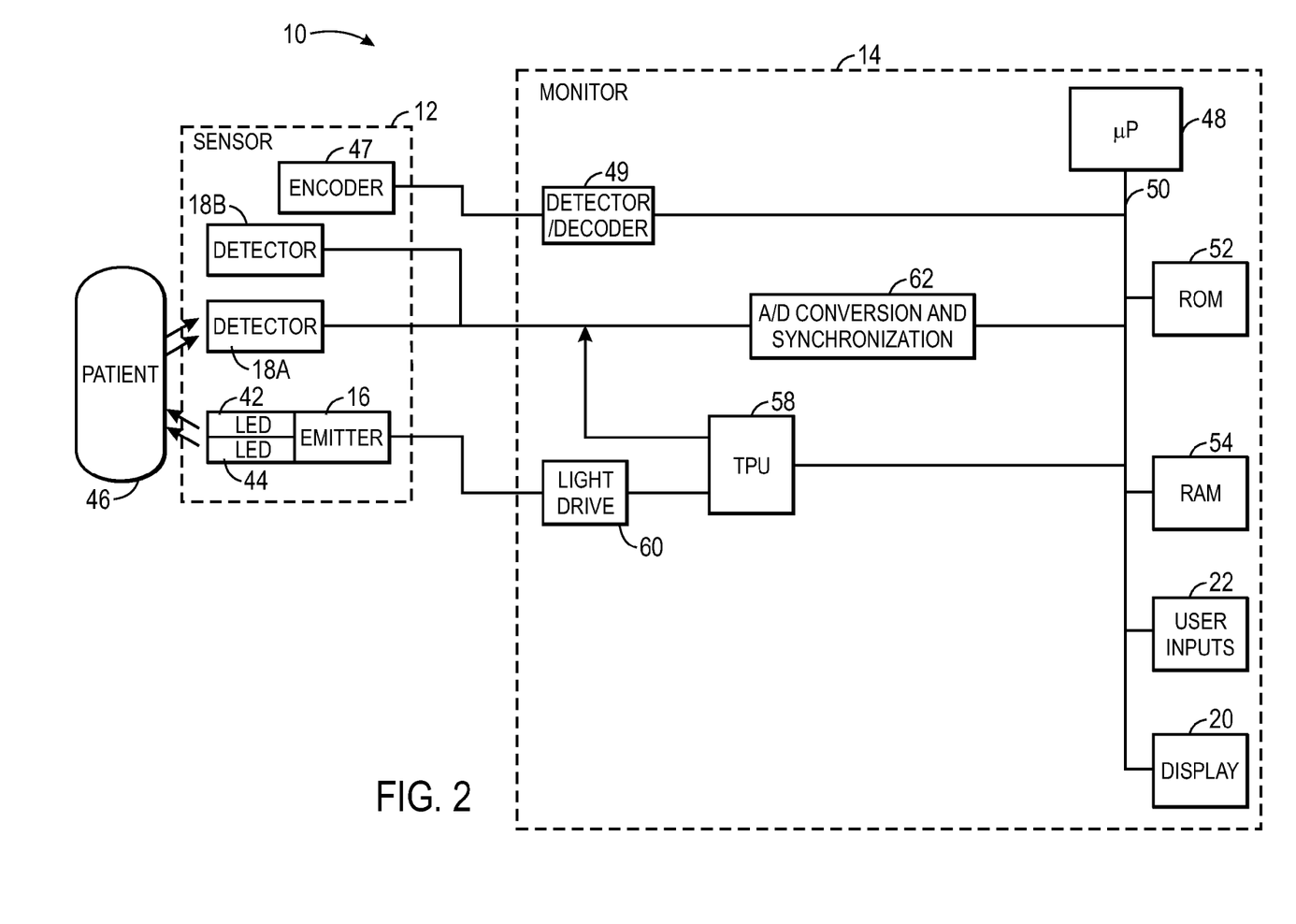
FIG. 2 is a block diagram of the monitoring system of FIG. 1, in accordance with an aspect of the present disclosure.

As provided herein, the sensor 12 may be configured to perform regional oximetry. Indeed, in one embodiment, the sensor 12 may be an INVOS® cerebral/somatic sensor available from Somanetics Corporation. In regional oximetry, by comparing the relative intensities of light received at two or more detectors, it is possible to estimate the blood oxygen saturation of hemoglobin in a region of a body. For example, a regional oximeter may include a sensor to be placed on a patient's forehead and may be used to calculate the oxygen saturation of a patient's blood within the venous, arterial, and capillary systems of a region underlying the patient's forehead (e.g., in the cerebral cortex). As illustrated in FIGS. 1 and 2, the sensor 12 may include the emitter 16 and the two detectors 18: one detector 18A that is relatively "close" to the emitter 16 and another detector 18B that is relatively "far" from the emitter 16. Light intensity of one or more wavelengths may be received at both the "close" and the "far" detectors 18A and 18B. Thus, the detector 18A may receive a first portion of light and the detector 18B may receive a second portion of light. Each of the detectors 18 may generate signals indicative of their respective portions of light. For example, the resulting signals may be contrasted to arrive at a regional saturation value that pertains to additional tissue through which the light received at the "far" detector 18B passed (tissue in addition to the tissue through which the light received by the "close" detector 18A passed, e.g., the brain tissue) when it was transmitted through a region of a patient (e.g., a patient's cranium). Surface data from the skin and skull is subtracted out to produce a regional oxygen saturation ($rSO_2$) value for deeper tissues.

Turning to FIG. 2, a simplified block diagram of the medical system 10 is illustrated in accordance with an embodiment. The sensor 12 may include optical components in the forms of the emitter 16 and detectors 18. The emitter 16 and the detectors 18 may be arranged in a reflectance or transmission-type configuration with respect to one another. However, in embodiments in which the sensor 12 is configured for use on a patient's forehead, the emitter 16 and detectors 18 may be in a reflectance configuration. An emitter 16 may also be a light emitting diode, superluminescent light emitting diode, a laser diode, or a vertical cavity surface emitting laser (VCSEL). An emitter 16 and the detectors 18 may also include optical fiber sensing elements. An emitter 16 may include a broadband or "white light" source, in which case the detectors 18 could include any of a variety of elements for selecting specific wavelengths, such as reflective or refractive elements or interferometers. These kinds of emitters and/or detectors would typically be coupled to the sensor 12 via fiber optics. Alternatively, the sensor 12 may sense light detected from the tissue is at a different wavelength from the light emitted into the tissue. Such sensors may be adapted to sense fluorescence, phosphorescence, Raman scattering, Rayleigh scattering and multi-photon events, or photoacoustic effects. In one embodiment, the emitter 16 may be configured for use in a regional saturation technique. To that end, the emitter 16 may include two light emitting diodes (LEDs) 42 and 44 that are capable of emitting at least two wavelengths of light, e.g., red or near infrared light. In one embodiment, the LEDs 42 and 44 emit light in the range of 600 nm to about 1000 nm. In a particular embodiment, the one LED 42 is capable of emitting light at 730 nm and the other LED 44 is capable of emitting light at 810 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In any suitable configuration of the sensor 12, the detectors 18A and 18B may be an array of detector elements that may be capable of detecting light at various intensities and wavelengths. In one embodiment, light enters the detector 18 (e.g., detector 18A or 18B) after passing through the tissue of the patient 46. In another embodiment, light emitted from the emitter 16 may be reflected by elements in the patient's tissue to enter the detector 18. The detector 18 may convert the received light at a given intensity, which may be directly related to the absorbance and/or reflectance of light in the tissue of the patient 46, into an electrical signal. That is, when more light at a certain wavelength is absorbed, less light of that wavelength is typically received from the tissue by the detector 18, and when more light at a certain wavelength is reflected, more light of that wavelength is typically received from the tissue by the detector 18. After converting the received light to an electrical signal, the detector 18 may send the signal to the monitor 14, where physiological characteristics may be calculated based at least in part on the absorption and/or reflection of light by the tissue of the patient 46.

In certain embodiments, the medical sensor 12 may also include an encoder 47 that may provide signals indicative of the wavelength of one or more light sources of the emitter 16, which may allow for selection of appropriate calibration coefficients for calculating a physical parameter such as blood oxygen saturation. The encoder 47 may, for instance, include a coded resistor, an electrically erasable programmable read only memory (EEPROM), or other coding device (such as a capacitor, inductor, programmable read only memory (PROM), RFID, parallel resident currents, or a colorimetric indicator) that may provide a signal to a microprocessor 48 related to the characteristics of the medical sensor 12 to enable the microprocessor 48 to determine the appropriate calibration characteristics of the medical sensor 12. Further, the encoder 47 may include encryption coding that prevents a disposable part of the medical sensor 12 from being recognized by a microprocessor 48 unable to decode the encryption. For example, a detector/decoder 49 may translate information from the encoder 47 before the processor 48 can properly handle it. In some embodiments, the encoder 47 and/or the detector/decoder 48 may not be present.

In certain embodiments, the sensor 12 may include circuitry that stores patient-related data (e.g., $rSO_2$ baseline) and provides the data when requested. The circuitry may be included in the encoder 47 or in separate memory circuitry within the sensor 12. Examples of memory circuitry include, but are not limited to, a random access memory (RAM), a FLASH memory, a PROM, an EEPROM, a similar programmable and/or erasable memory, any kind of erasable memory, a write once memory, or other memory technologies capable of write operations. In one embodiment, patient-related data, such as the $rSO_2$ baseline, trending data, or patient monitoring parameters, may be actively stored in the encoder 47 or memory circuitry. As the patient 46 and sensor 12 travel through a medical facility, such as a hospital, and consequently communicate with different monitors 14, the patient-related data (e.g., $rSO_2$ baseline) may be read from the encoder 47 and displayed on the monitor display 20 for viewing or used by the monitor 14 for other purposes. Examples of patient-related data that can be stored in the encoder 47 or memory circuitry are discussed in detail below.

Returning to FIG. 2, signals from the detector 18 and/or the encoder 47 may be transmitted to the monitor 14. By way of example, the monitor 14 shown in FIG. 2 may be an INVOS® System monitor 14 available from Somanetics Corporation. The monitor 14 may include one or more processors 48 coupled to an internal bus 50. Also connected to the bus 50 may be a ROM memory 52, a RAM memory 54, and the display 20. A time processing unit (TPU) 58 may provide timing control signals to light drive circuitry 60, which controls when the emitter 16 is activated, and if multiple light sources are used, the multiplexed timing for the different light sources. The received signal from the detector 18 may be passed through analog-to-digital conversion and synchronization 62 under the control of timing control signals from the TPU 58. Specifically, the signal may undergo synchronized demodulation and optionally amplification and/or filtering. For example, the LEDs 42 and 44 may be driven out-of-phase, sequentially and alternatingly with one another (i.e., only one of the LEDs 42 and 44 being driven during the same time interval) such that the detector 18 receives only resultant light spectra emanating from one LED at a time. Demodulation 62 of the signal enables the data associated with the LEDs 42 and 44 to be distinguished from one another. After demodulation, the digital data may be downloaded to the RAM memory 54.

In an embodiment, based at least in part upon the received signals corresponding to the light received by detector 18, the processor 48 may calculate the oxygen saturation using various algorithms. These algorithms may use coefficients, which may be empirically determined. For example, algorithms relating to the distance between an emitter 16 and various detector elements in a detector 18 may be stored in the ROM memory 52 and accessed and operated according to processor 48 instructions.

Furthermore, one or more functions of the monitor 14 may also be implemented directly in the sensor 12. For example, in some embodiments, the sensor 12 may include one or more processing components capable of calculating the physiological characteristics from the signals obtained from the patient 46. In accordance with the present techniques, the sensor 12 may be configured to provide desired contact between the patient 46 and the detector 18, and/or the emitter 16. The sensor 12 may have varying levels of processing power, and may output data in various stages to the monitor 14, either wirelessly or via the cable 26. For example, in some embodiments, the data output to the monitor 14 may be analog signals, such as detected light signals (e.g., oximetry signals or regional saturation signals), or processed data.

Figure 3:
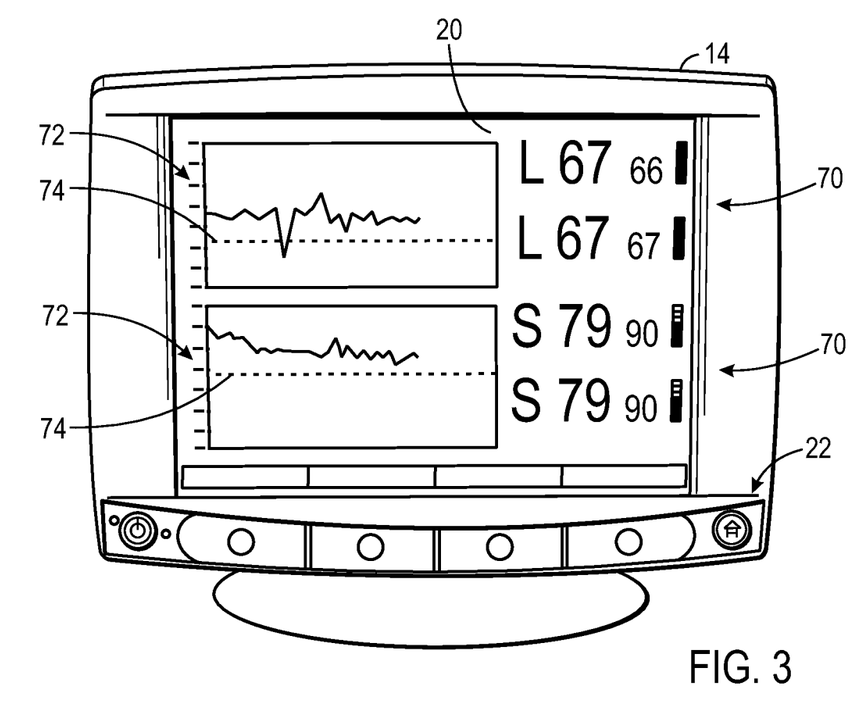
FIG. 3 is a front view of an embodiment of a regional saturation monitor, in accordance with an aspect of the present disclosure.

The use of two or more sensors 12 for dual or bilateral examination may provide useful comparative display formats, as illustrated in FIG. 3, for example. In the arrangement shown in FIG. 3, the output from each sensor 12 is separately processed to provide a particular regional oxygen saturation value, and these regional values are separately displayed on the monitor display 20 as both a numeric or other such quantified value 70, constituting basically an instantaneous real-time value, and as a point in a graphical plot 72, representing a succession of such values taken over time. As illustrated, the plots or graphs 72 may advantageously be disposed one above the other in direct alignment, for convenient examination and comparison. While the instantaneous numeric displays 70 provide useful information, particularly when arranged in the manner illustrated in FIG. 3, the graphical trace displays 72 also provide useful information by directly showing the ongoing trend, and doing so in a contrasting, comparative manner, as well as showing the actual or relative values.

As shown in FIG. 3, one or more baselines 74 may be shown in each of the graphical plots 72. The baseline 74 may correspond to regional oxygen saturation ($rSO_2$) data collected at a certain time or over a certain period. When the baseline 74 corresponds to $rSO_2$ data collected over a period, the baseline 74 may typically correspond to an average or mean value of the collected data. The caregiver may be able to quickly and easily compare the baseline 74 against current $rSO_2$ data (e.g., a trend line) or $rSO_2$ data collected at a different time or period by simply looking at the display 14. Thus, displaying the baseline 74 on the graphical plot 72 may facilitate decision making by the caregiver. For example, the baseline 74 may be based on $rSO_2$ data collected prior to a medical procedure, such as surgery. During the medical procedure, the baseline 74 may continue to be displayed on the graphical plot 72, allowing the caregiver to compare current $rSO_2$ data (e.g., a trend line) to the baseline 74 and make necessary adjustments during the medical procedure. After the medical procedure is complete, the baseline 74 may continue to be shown on the graphical plot 72, enabling the caregiver to adjust post-procedure treatment and care as necessary. In certain embodiments, the monitor 14 may be configured to enable the caregiver to select a different baseline 74 to be displayed. For example, after the medical procedure is completed, a post-procedure baseline 74 may be more useful for the caregiver. In addition, as discussed above, the baseline 74 may be stored in the sensor 12. Thus, the value of the baseline 74 may travel with the patient as long as the sensor 12 remains with the patient. Thus, the sensor 12 may enable the same baseline 74 to be displayed on different monitors 14 located throughout the medical facility.

Figure 4:
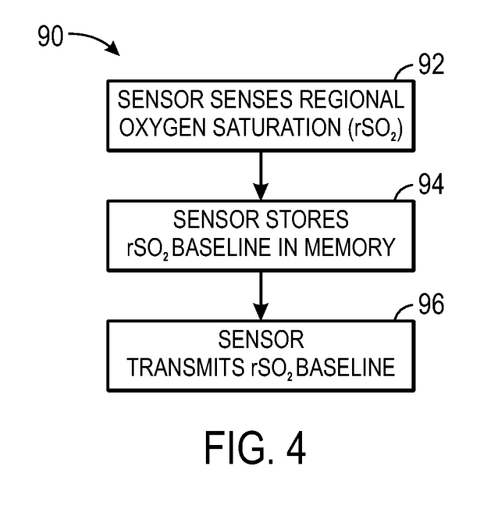
FIG. 4 is a process flow diagram of an embodiment of a method for using a sensor to store and provide a regional oxygen saturation ($rSO_2$) baseline.

As discussed above, embodiments of the sensor 12 enable the baseline 74 to travel with the patient. Referring now to FIG. 4, an embodiment of a method 90 for using the sensor 12 (e.g., an INVOS® sensor) to store and provide physiological data, such as the baseline 74, is shown. The method 90 begins with the sensor 12 sensing a regional oxygen saturation ($rSO_2$). For example, the sensor 12 may be affixed to the patient and provided with electrical power to obtain $rSO_2$ values (block 92). The sensor 12 may then store the $rSO_2$ baseline 74 in the sensor 12 (block 94). As discussed above, the $rSO_2$ baseline 74 may be stored in the encoder 47 or in memory circuitry within the sensor 12. In certain embodiments, the sensor 12 may store the baseline 74 as a series of $rSO_2$ values (e.g., a trend line). In other embodiments, the sensor 12 may determine the average of the $rSO_2$ values over time and store the baseline 74 as the average value of the collected $rSO_2$ values. After storing the $rSO_2$ baseline 74, the sensor 12 may then transmit the $rSO_2$ baseline (block 96). For example, the sensor 12 may transmit the $rSO_2$ baseline 74 to the monitor 14 coupled to the sensor 12. Thus, the $rSO_2$ baseline 74 may be available for viewing on the display 20 of the monitor 14 by the caregiver. In certain embodiments, the monitor 14 may receive the $rSO_2$ values (e.g., trend line) from the sensor 12 and determine an average (e.g., a horizontal line) of the $rSO_2$ values to be displayed as the baseline 74. Alternatively, the monitor 14 may display the baseline 74 as the trend line of the $rSO_2$ values stored by the sensor 12. In further embodiments, the monitor 14 receives and displays the baseline 74 as the average value of the $rSO_2$ values determined by the sensor 12.

Figure 5:
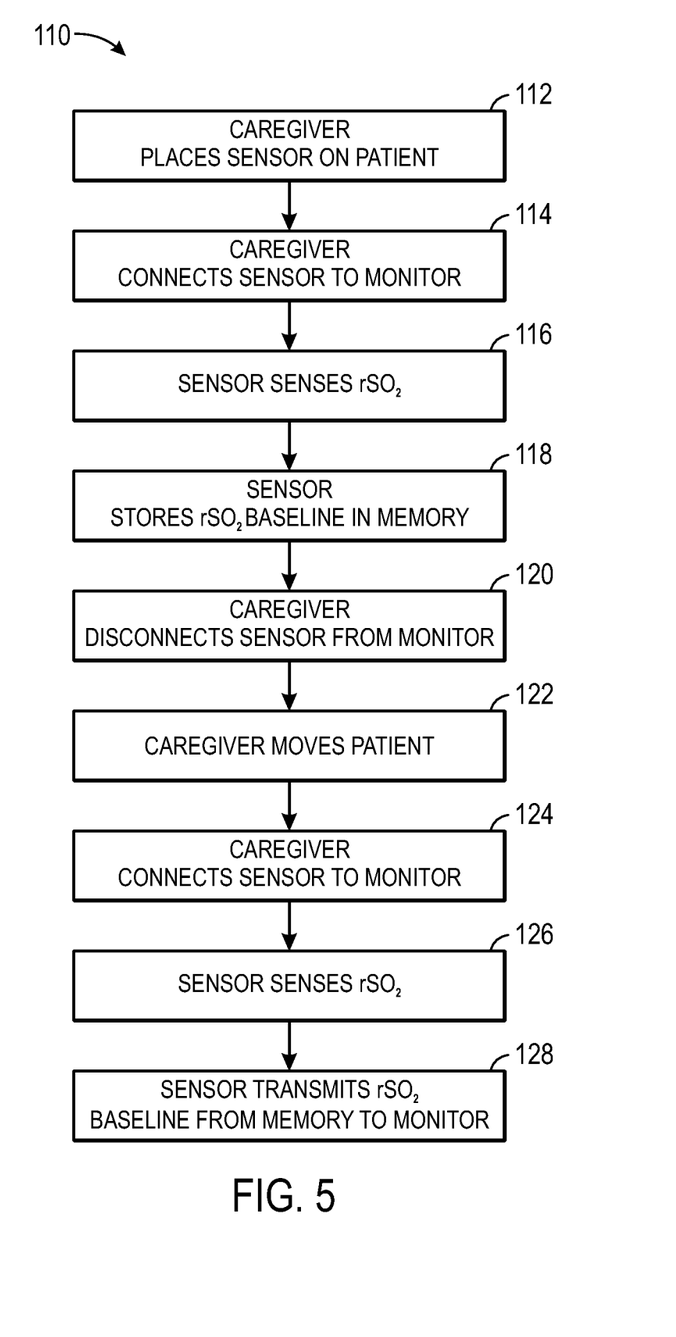
FIG. 5 is a process flow diagram of an embodiment of a method for using a sensor with a plurality of monitors to store and provide $rSO_2$ baseline values.

As discussed above, the patient may be moved or undergo medical treatment between storing the $rSO_2$ baseline 74 in the sensor 12 and transmitting the $rSO_2$ baseline 74 to the monitor 14. To illustrate how the sensor 12 may be used to store and provide the $rSO_2$ baseline 74 in these situations, FIG. 5 shows an embodiment of a method 110 for using the sensor 12 with a plurality of different monitors 14. The method 110 begins with the caregiver placing the sensor 12 on the patient (block 112). Next, the caregiver may connect the sensor 12 to the monitor 14 (block 114). In other embodiments, the sensor 12 may communicate wirelessly with the monitor 14. The sensor 12 may begin to sense $rSO_2$ data of the patient (block 116). The $rSO_2$ data (e.g., trend line) may be transmitted and displayed on the monitor 14. In addition, the sensor 12 may store the $rSO_2$ data as the $rSO_2$ baseline 74 in the sensor 12 (block 118). As discussed above, the $rSO_2$ baseline 74 may be stored in the encoder 47 or in memory circuitry within the sensor 12. In addition, the $rSO_2$ baseline 74 may be stored as a series of $rSO_2$ values or as an average of a series of $rSO_2$ values. During the previous steps, the patient may be located in a pre-treatment room (e.g., an emergency room, patient room, or pre-operating room). When the patient is moved from the pre-treatment room, the caregiver may disconnect the sensor 12 from the monitor 14 (block 120). Next, the caregiver may move the patient to a treatment room (e.g., operating room) or any other room within the medical facility (block 122). While the patient is being moved, the sensor 12 may not be connected to a monitor 14; however, the $rSO_2$ baseline 74 remains stored in the sensor 12. Next, the caregiver may connect the sensor 12 to another monitor 14 located in the treatment room (block 124). The sensor 12 may then begin sensing $rSO_2$ data of the patient (block 126). The current $rSO_2$ data may be transmitted from the sensor 12 to the monitor 14 for viewing on the display 20. In addition, the sensor 12 may transmit the $rSO_2$ baseline 74 from the encoder 47 or memory circuitry within the sensor 12 to the monitor 14 to be displayed in the graphical plot 72 of the display 20 (block 128). As discussed above, the $rSO_2$ baseline 74 may be displayed as a trend line or as an average value (e.g., a horizontal line). In addition, either the sensor 12 or the monitor 14 may determine the average value of the collected $rSO_2$ data. Thus, the caregiver may be able to compare the current $rSO_2$ data with the $rSO_2$ baseline 74 determined while the patient was in the pre-treatment room. The steps described above may then be repeated when the patient is moved from the treatment room to a post-treatment room (e.g., intensive care unit or recovery room) or other room in the medical facility.

In certain embodiments, additional features may be included in the patient monitoring system 10 to facilitate usage and display of the baselines 74. For example, when the sensor 12 is connected to the monitor 14, the caregiver may be prompted whether to have the sensor 12 transmit the baseline 74 to the monitor 14. Thus, in certain situations, the caregiver may decide not to display the baseline 74 on the monitor 14. For example, when the sensor 12 is briefly disconnected and reconnected from the same monitor 14, the baseline 74 may not be useful information to be viewed by the caregiver. In addition, the sensor 12 may store several baselines 74 (e.g., pre-treatment baseline, treatment baseline, post-treatment baseline) and the caregiver may use the monitor 14 to select the appropriate one or more baseline 74 for viewing. For example, the sensor 12 may store timestamps or other labels together with each baseline 74 that are shown on the display 20 to enable the caregiver to distinguish one baseline 74 from another.

In further embodiments, the caregiver may be able to delete or erase baselines 74 from the sensor 12 when no longer needed. For example, the encoder 47 or the memory circuitry may be erased and overwritten multiple times. In certain embodiments, the baseline 74 may be erased from the encoder 47 or memory circuitry each time a sensor 12 is used on a new patient (e.g., when user input to the monitor 14 indicates a new patient). This memory characteristic may be advantageous, for example, with nondisposable sensors that may be used multiple times on multiple patients. Alternatively, the baseline 74 encoded into the encoder 47 or memory circuitry may be permanent and non-erasable. In a specific embodiment, to preserve the baseline 74 and prevent accidental erasure, the encoder 47 or memory circuitry may be written to only once. This memory characteristic also prevents erasure of the baseline 74 during sensor operation. In further embodiments, the sensor 12 may be configured to store only a specified number of baselines 74 or amount of baseline information. Once the sensor 12 reaches the limit, it may be disposed of to prevent baseline information from one patient from being accidentally used with another patient.

In other embodiments, the sensor 12 may be configured to be able to detect when the sensor 12 has been removed or dislodged from the patient (e.g., a poor connection). Data collected by the sensor 12 when it is not attached to the patient or improperly attached to the patient may be unhelpful, and may negatively affect the value of the baseline 74 stored in the sensor 12. In certain embodiments, the sensor 12 may include a sacrificial piece of adhesive or other active means for detecting removal or dislodging of the sensor 12 from the patient. For example, electrical contacts disposed on the sensor 12 may indicate lack of electrical continuity when the sensor 12 is removed from the patient. The detection of movement or removal of the sensor 12 from the patient may be stored in the encoder 47 or memory circuitry within the sensor 12. Thus, the caregiver may be able to select the physiological data used to determine the baseline 74 and remove data that may have been collected when the sensor 12 was not attached or improperly attached to the patient. Therefore, the baseline 74 may provide to the caregiver an accurate indication of the $rSO_2$ of the patient during the monitored period.

In yet further embodiments, the sensor 12 may be configured to store a patient identification code (patient ID), such as a unique number carried along in the sensor 12, so that the $rSO_2$ baseline 74 is associated with the correct patient. Thus, as the patient is moved from one location to another, subsequent caregivers can verify that the $rSO_2$ baseline 74 stored in the sensor 12 was obtained from that particular patient. For example, the caregiver can check that the patient ID stored in the sensor 12 matches the patient ID on the patient's chart and other paper documentation. In addition, the sensor 12 may be interfaced with a hospital computer network that maintains a database of patient ID numbers to verify the identity of the patient. Correlating the $rSO_2$ baseline 74 to a particular patient may be important because the $rSO_2$ baseline 74 may be different from one patient to another.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed.

Rather, the various embodiments may cover all modifications, equivalents, and alternatives falling within the spirit and scope of the disclosure as defined by the following appended claims.

What is claimed is:

1. A regional oximetry sensor, comprising:
a light emitting element disposed on a tissue contacting surface of the regional oximetry sensor and configured to emit light;
a first light detector and a second light detector each disposed on the tissue contacting surface and each configured to detect the light, wherein the first light detector is disposed at a first distance from the light emitting element and the second light detector is disposed at a second distance from the light emitting element, and wherein the first distance is greater than the second distance;
a memory device; and
processing circuitry associated with the memory device, wherein the processing circuitry is configured to:
determine a baseline based at least in part on the detected light, wherein the baseline comprises a plurality of $rSO_2$ measurements of a patient obtained by the regional oximetry sensor over a period of time, and wherein the plurality of $rSO_2$ measurements are based at least in part on the detected light;
store the baseline within the memory device;
transmit the baseline to a display of a regional oximetry monitor when the regional oximetry sensor is coupled to the regional oximetry monitor;
detect removal or dislodging of the regional oximetry sensor from the patient; and
label the baseline with a timestamp associated with the detected removal or dislodging of the regional oximetry sensor from the patient and store the labeled baseline within the memory device.

2. The sensor of claim 1, wherein the processing circuitry is configured to determine an average $rSO_2$ value of the plurality of $rSO_2$ measurements obtained by the regional oximetry sensor over the period of time.

3. The sensor of claim 1, wherein the processing circuitry is configured to retain the baseline in the memory device when the regional oximetry sensor is disconnected from the regional oximetry monitor or is removed from the patient.

4. The sensor of claim 1, wherein the processing circuitry is configured to store a plurality of timestamps associated with the plurality of $rSO_2$ measurements in the memory device.

5. The sensor of claim 1, wherein the processing circuitry is configured to store a plurality of baselines over a plurality of time periods.

6. The sensor of claim 5, wherein the regional oximetry monitor prompts the caregiver to select a desired baseline of the plurality of baselines when the regional oximetry monitor is coupled to the regional oximetry sensor.

7. The sensor of claim 5, wherein the processing circuitry is configured to store a plurality of timestamps with each of a plurality of baselines stored in the memory device.

8. The sensor of claim 1, wherein the processing circuitry is configured to calculate a cerebral saturation value or a somatic saturation value based at least in part on the received light.

9. The sensor of claim 1, wherein the processing circuitry is configured to associate a patient identification code with the baseline to correctly identify the patient from among a plurality of patients.

10. A method, comprising:
emitting light from a light emitting element disposed on a tissue contacting surface of a regional oximetry sensor;
detecting a first portion of the light with a first detector and a second portion of the light with a second detector, wherein the first and second detectors are disposed on the tissue contacting surface of the regional oximetry sensor, wherein the first light detector is disposed at a first distance from the light emitting element and the second light detector is disposed at a second distance from the light emitting element, and wherein the first distance is greater than the second distance;
determining a baseline comprising a plurality of regional oxygen saturation ($rSO_2$) measurements over a period of time, wherein the plurality of $rSO_2$ measurements are based at least in part on the first and second portions of detected light, and wherein the baseline comprises an average $rSO_2$ value of the plurality of $rSO_2$ measurements over the period of time; and
transmitting the baseline to a display of a first regional oximetry monitor when the regional oximetry sensor is coupled to the first regional oximetry monitor.

11. The method of claim 10, comprising removing or dislodging the regional oximetry sensor from the patient and uncoupling the regional oximetry sensor from the first regional oximetry monitor.

12. The method of claim 11, comprising labeling the baseline with a timestamp associated with the detected removal or dislodging of the regional oximetry sensor from the patient and storing the labeled baseline within the memory device.

13. The method of claim 12, comprising transmitting the labeled baseline to a second regional oximetry monitor when the second regional oximetry monitor is coupled to the regional oximetry sensor.

14. The method of claim 10, comprising displaying the baseline on a display of the regional oximetry when the regional oximetry sensor is coupled to the first regional oximetry monitor.

15. The method of claim 10, comprising determining a plurality of baselines over a plurality of periods of time.

16. The method of claim 15, comprising prompting a caregiver to select a desired period of time among the plurality of periods of time, and transmitting the baseline associated with the desired period of time to the first regional oximetry monitor.

17. The method of claim 10, comprising calculating a cerebral saturation value or a somatic saturation value based at least in part on the received light.

18. A system comprising:
a regional oximetry sensor, comprising:
a light emitting element disposed on a tissue contacting surface of the regional oximetry sensor and configured to emit light;
a first light detector and a second light detector each disposed on the tissue contacting surface and each configured to receive the light, wherein the first light detector is disposed at a first distance from the light emitting element and the second light detector is disposed at a second distance from the light emitting element, and wherein the first distance is greater than the second distance;
a memory device; and
first processing circuitry associated with the memory device, wherein the first processing circuitry is configured to:

determine a baseline based at least in part on the received light, wherein the baseline comprises a plurality of $rSO_2$ measurements of a patient obtained by the regional oximetry sensor over a period of time, and wherein the plurality of $rSO_2$ measurements are based at least in part on the detected light; and store the baseline within the memory device; and a regional oximetry monitor configured to be coupled to the regional oximetry sensor, wherein the regional oximetry monitor comprises:

second processing circuitry configured to receive the baseline from the regional oximetry sensor when the regional oximetry monitor is coupled to the regional oximetry sensor, and wherein the second processing circuitry is configured to display the baseline on a display of the regional oximetry monitor.

19. The system of claim 18, wherein the first processing circuitry is configured to retain the baseline within the memory device until the regional oximetry sensor is coupled to the regional oximetry monitor.

20. The system of claim 19, wherein the first processing circuitry is configured to erase the baseline from the memory device after the regional oximetry sensor is coupled to the regional oximetry monitor.

* * * * *